United States Patent [19]

Petruson

[11] Patent Number: 5,479,944

[45] Date of Patent: Jan. 2, 1996

[54] NASAL DEVICES

[75] Inventor: Bjorn Petruson, Goteborg, Sweden

[73] Assignee: Patent Development & Investment S.A., Luxembourg

[21] Appl. No.: 701,621

[22] Filed: May 14, 1991

Related U.S. Application Data

[63] Continuation of Ser. No. 391,010, May 17, 1989, abandoned.

[51] Int. Cl.⁶ ........................................... A61F 5/37
[52] U.S. Cl. ............................................. 128/858; 606/196
[58] Field of Search ................. 128/206.11, 202.17, 128/858, 89 A, 114.1; 606/196, 198, 199

[56] References Cited

U.S. PATENT DOCUMENTS

| | | | |
|---|---|---|---|
| 701,538 | 6/1902 | Carence | 128/206.11 |
| 1,134,993 | 4/1915 | Bye | 128/202.17 |
| 1,256,188 | 2/1918 | Wilson | 606/199 |
| 1,322,375 | 11/1919 | Un | 128/206.11 |
| 1,950,926 | 10/1932 | Lobl | 128/203.22 |
| 2,055,855 | 9/1936 | Weaver | 128/206.11 |
| 2,243,360 | 5/1941 | Slatis | 128/206.11 |
| 2,264,153 | 2/1940 | Rowe | 128/204.12 |
| 2,274,997 | 3/1942 | Thurman | 128/858 |
| 2,277,390 | 3/1941 | Crespo | 128/204.12 |
| 2,426,161 | 8/1947 | Biederman | 128/206.11 |
| 2,509,157 | 5/1950 | Lind | 128/89 A |
| 2,674,245 | 4/1954 | Tanditter | 128/206.11 |
| 2,715,904 | 8/1955 | Hill | 128/203.22 |
| 3,027,897 | 4/1962 | Carofiglio | 128/202.17 |
| 3,905,335 | 9/1975 | Kapp | 128/206.11 |
| 4,201,217 | 5/1980 | Slater | 606/199 |
| 4,220,150 | 9/1980 | King | 128/206.11 |
| 4,221,217 | 9/1980 | Amezcua | 128/206.11 |
| 4,267,831 | 5/1981 | Aguilar | 128/206.11 |
| 4,327,719 | 5/1982 | Childers | 128/206.11 |
| 4,592,357 | 6/1986 | Ersek | 606/199 |

FOREIGN PATENT DOCUMENTS

| | | | |
|---|---|---|---|
| 242553 | 5/1961 | Australia . | |
| 394505 | 3/1909 | France . | |
| 630889 | 12/1927 | France . | |
| 1001434 | 5/1946 | France . | |
| 1046299 | 12/1951 | France . | |
| 1182602 | 9/1957 | France . | |
| 1351537 | 12/1962 | France . | |
| 0381127 | 9/1923 | Germany . | |
| 381127 | 9/1923 | Germany . | |
| 882601 | 7/1953 | Germany . | |
| 1244146 | 6/1970 | Spain . | |
| 354998 | 4/1931 | United Kingdom . | |
| 520491 | 4/1940 | United Kingdom . | |
| 786488 | 4/1955 | United Kingdom . | |
| 0748326 | 4/1956 | United Kingdom . | 606/199 |
| 0768488 | 2/1957 | United Kingdom . | 606/199 |
| 2126101 | 3/1984 | United Kingdom . | |

*Primary Examiner*—Michael A. Brown
*Attorney, Agent, or Firm*—Fishman, Dionne & Cantor

[57] ABSTRACT

Devices for improving nasal breathing and to nasal drug delivery devices having two end portions of a resilient material in the form of relatively thin tabs, perferably having a gentle curvature, interconnected by a resilient member. Upon bending of the connecting member, the two end tabs can be positioned in respective nostrils where they will be biased outwardly against the nasal side walls, the outward biasing force being sufficient to locate the device in the nose and to dilate the anterior part of each nasal cavity by an amount to improve nasal breathing. No part of the device is grippingly engaged with the septum and a substantial free passage for air flow remains between the septum wall and the nasal side wall-contacting face of each end tab.

28 Claims, 3 Drawing Sheets

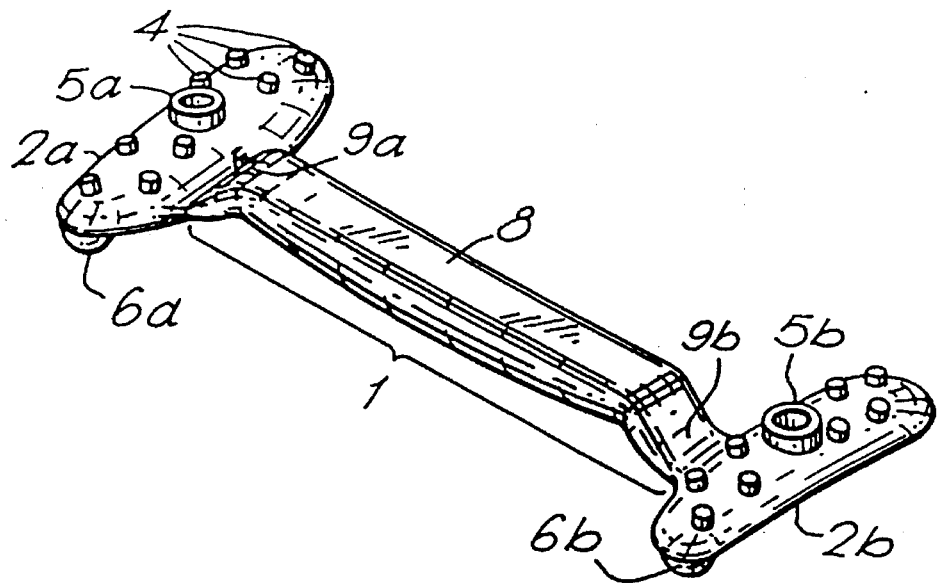
FIG.5.
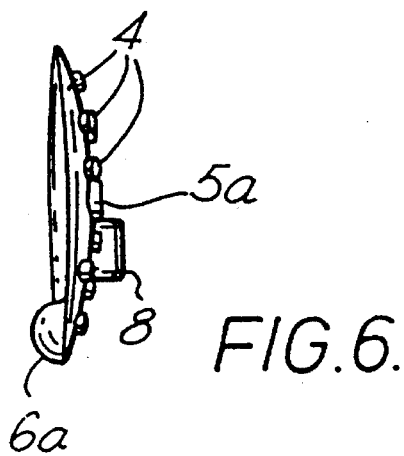
FIG.6.
FIG.7.
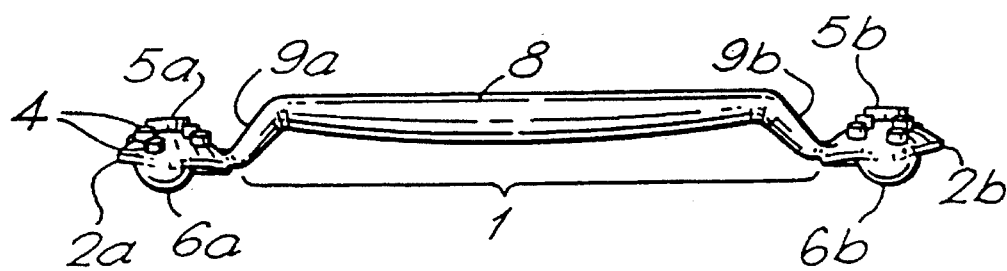
FIG.8.
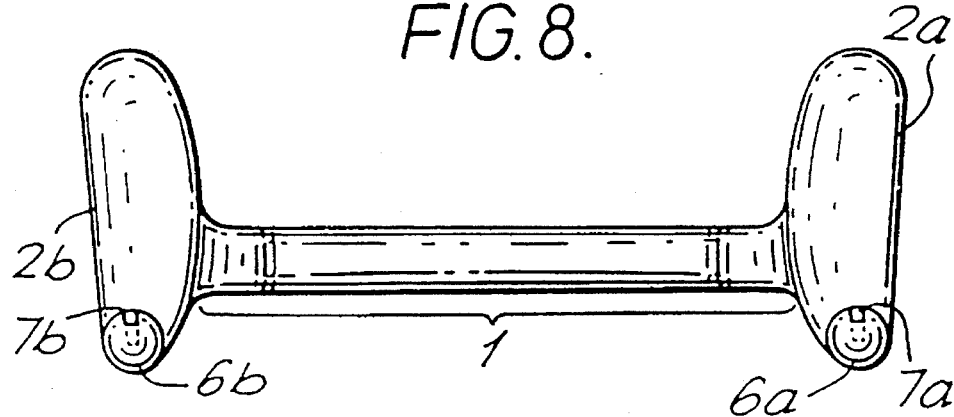

NASAL DEVICES

This application is a continuation of 07/391,010, filed May 17, 1989, now abandoned.

The present specification relates to nasal devices. In particular, it relates to devices for improving nasal breathing capacity and to nasal drug-delivery devices.

The nose is divided into two cavities by a thin wall or septum in the mid-line. The side walls are irregular due to three baffles important for the air condition function and all the walls are covered by mucous membranes which have a large ability to warm and humidify the inspired air. If breathing through the nose is impaired so that breathing through the mouth becomes necessary, "conditioning" of the inspired air occurs less efficiently and hence drying of the mucosa in the throat and bronchi may result. In many patients with asthma, the bronchial mucosa is highly susceptible to inhalation of cold air and it is thus particularly desirable for such individuals to breathe only through the nose. If the anterior part of each nasal cavity is dilated, the ability to breathe through the nose increases significantly.

A further undesirable effect related to airway obstruction in the nose is snoring. A snoring sound is generated during inspiration when there is an airway obstruction in the nose or throat which is overcome by deep breathing resulting in vibration of the soft tissues in the palate and throat and is a very common phenomenon in sleeping individuals. About 20% of normal adults snore habitually, the phenomenon being more common in men than women and in people aged over 40. Despite this, no device for preventing snoring has as yet found wide-spread acceptance. The most commonly used method for stopping an individual snoring remains to disturb them so that their breathing pattern is modified. However, when the person falls fully asleep again snoring is liable to recurr.

An alternative means of preventing snoring is to dilate the anterior part of each nasal cavity so that nasal breathing capacity is improved. While devices for insertion in the nose to improve nasal breathing capacity have previously been disclosed none of these, however, are suitable for long term every day use either by individuals with a snoring problem or asthma sufferers in view of liability to cause unacceptable discomfort and/or the increase in size of the nasal cavities being off-set to a large degree by the size of the portions of the device inserted therein. Moreover, some of these devices are unacceptable from an aesthetic point of view for general daytime use by asthma sufferers.

GB-A-1244146, for example, discloses a device for facilitating nasal breathing comprising two spherical or ellipsoidal frames for insertion into the nostrils, the frames being formed of a plurality of interconnected rings of a non-oxidisable metal or rigid plastic material and being connected by a loose linkage of further such rings. When fitted into a nose, each spherical or ellipsoidal frame of a device of this type fills much of the lower part of the nasal cavity into which it is inserted and contacts both the septum and the interior surface of the side wall. The frames are liable to cause irritation, particularly if they contact the sensitive nasal mucosa, and may give rise to nose bleeds and ulcers. These same problems are shared by devices more recently disclosed in GB-A-2126101 for assisting nasal breathing, wherein the end pieces inserted into the nasal cavities are helical coils formed, for example, from lightly tempered stainless steel and joined by a simple loop of the same material which fits around the septum. The helical coils, when inserted into the nostrils of an individual, contact both the nasal side walls and the septum and significantly disrupt air flow through the anterior part of each nasal cavity. Such devices cannot be maintained in the nose with a high degree of comfort for a long period of time and despite their ease of construction have not been widely used either for alleviation of snoring or for use in treatment of other conditions where an increase of nasal breathing is desirable.

Devices are also known for fitment in the nose of an individual which are intended to have the dual function of improving nasal breathing capacity and enabling delivery of drugs into the nasal cavities, but none of these have found widespread favour for use in medical practice, e.g. in the treatment of asthma sufferers. For example, GB-A-768488 discloses nasal drug delivery devices consisting of a generally U-shaped resilient strip with two arms for fitment in the nasal cavities of an individual, the two arms having at the upper end a closed oval loop with claws to hold a drug-impregnated absorbent material, e.g. gauze or cotton wool. Such devices undesirably depend for retention in the nose both upon outward pressure of a portion of each arm against the adjacent nasal side wall and upon a pincenez formed by a lower region of each arm which grips the septum. Moreover, when a device of this type is employed in the drug-loaded form, the protrudance of the drug-holding portions outwards from the nasal side walls towards the septum substantially reduces the free passageway for air flow through the anterior part of each nasal cavity. Nasal drug delivery devices which depend for retention in the nose upon contact with both the septum wall and the interior of the nasal side walls are also disclosed in U.S. Pat. No. 2,243, 360. In the case of these devices, two casings for holding a medicament, which are shaped respectively to fit the lower internal section of a human right and left nostril, are engaged with both the septum and nasal side walls by means of a resilient bridge member interconnecting the two casings. When such a device is fitted in the nose, as with the drug-delivery devices of GB-A-768488, increase in nasal air flow is, however, considerably restricted by partial obstruction of the nasal cavities.

Nasal drug delivery devices of the pincenez-type which when fitted in the nose grippingly engage with the interior nasal septum wall separating the two nasal cavities are additionally disclosed in CH-A-340190.

Further nasal drug delivery devices are known, which are intended to provide some improvement of nasal breathing capacity and which depend for retention in the nose solely or at least principally upon contact of end portions with the nasal side walls. Representative of such devices are nasal drug delivery devices disclosed in FR-A-1001434 and DE-PS-381127 consisting of two drug-holding, perforated capsules connected by a resilient member, which when bent to insert the end capsules into the nasal cavities of an individual causes the end capsules to be pressed outwardly against the nasal size walls. Because, however, of the bulbous shape of the drug containers the increase in nasal cavity size is severely negated and such devices are not favourable for retention in the nose for long periods.

The majority of known nasal drug delivery devices when appropriately positioned in the nose of an individual in fact provide little or no increase in nasal breathing capacity by virtue of dilation of the nasal cavities and some even significantly reduce nasal breathing capacity as a result of the shape of the nasally-inserted portions. Such devices are exemplified by the devices disclosed in GB-A-520491, DE-PS-882601, FR-A-394505, FR-A-1351537, FR-A-1182602, FR-A-630889, FR-A-1046299, U.S. Pat. No. 1,950,926, U.S. Pat. No. 2,264,153, U.S. Pat. No. 2,277,390, U.S. Pat. No. 2,715,904 and GB-A-354998.

There is thus a need for improved devices for facilitating nasal breathing, with or without the capability for nasal drug delivery, which combine a high degree of comfort with a high degree of effectiveness in increasing nasal cavity size and which are sufficiently unobtrusive for every day use. Such devices provide the basis for the present specification.

There is thus disclosed a device which represents an improvement over GB-A-768488, in which there is disclosed a device for positioning in the nose to improve nasal breathing comprising two end portions interconnected resiliently so that when positioned in respective nostrils the end portions are biased outwardly against the nasal side walls. Having regard to this particular prior art, the device disclosed herein is characterised in that the said end portions are in the form of relatively thin tabs of a resilient material, the outward biasing force is sufficient to locate the device in the nose and to dilate the anterior part of each nasal cavity by an amount to improve nasal breathing and no part of the device is grippingly engaged with the septum.

The use of flat tabs means that a substantial free passage for air flow will remain between the septum wall and the non-nasal side wall contacting face of each of the said end portions. Furthermore, by having flat tabs which are resilient, comfort is increased and the area of engagement with the nasal side wall is increased. This makes it possible to dispense with other location means, such as engagement with the septum as in the case of the devices of GB-A-768488.

In preferred embodiments, the length of extension of the end tabs into the nasal cavities will be chosen such that the end tabs avoid contact with the sensitive nasal mucosa. Importantly, by virtue of the fact that such a device is retained in the nasal cavities solely or at least principally by substantially even pressure outwards via the end tabs against the nasal side walls below the mucosa, it may be fitted in the nose for long periods of time, e.g. overnight, without significant discomfort and without liability to cause nose bleeds or ulcers. Moreover, the adaptation of the end tabs to fit closely up against the nasal side walls when correctly inserted in the nose greatly facilitates increase of air flow. Devices of this type will have a high degree of patient acceptability and their manner of insertion can be readily learnt, even by young children.

The end tabs are desirably about 1–2 mm in thickness and interconnected by a narrow resilient member, for example about 4–5 mm in width and preferably thicker at the centre than at either end. The precise shape of each end tab will be chosen having regard to the effect required and the nose of the user. It is particularly desirable for the end tabs to have a gentle curvature, preferably with a maximum depth of curvature of about 1–2 mm, in which case when the device is correctly inserted into the nose, the convex faces of the end tabs should contact the nasal side walls.

Generally, the maximum length of extension of the end tabs into the nasal cavities will be about 15–20 mm and the maximum width of each end tab about 6–10 mm. In the case of a large male nose, for example, the maximum length of extension of each end tab into its respective nasal cavity will typically be about 17–20 mm and the maximum width of each end tab will be about 10 mm. In the case of a small child, these dimensions will typically be reduced for example to about 15–17 mm and about 6–8 mm respectively.

Preferably, at their lower ends the tabs will extend below the connecting member to form a tapering bottom portion, generally about 4–7 mm in length and preferably having a convexly-curved edge, which is intended to contact the floor of the nasal cavity thus assisting retention of the device in the nose. In order to assist retention of the device in the nose, gripping means may also be provided on the nasal side wall-contacting face of each of the end tabs so as to enhance engagement with the nasal side wall. Thus, a plurality of small circular protruberances or suction cups, generally about 1 mm in diameter and about 1 mm in length, may be provided on the nasal side wall-contacting faces of the end tabs. Generally, such protruberances or suction cups will be spaced as far as possible at substantially regular intervals.

The top of each end tab will generally either be convexly-curved or a substantially straight sloping edge. In the latter case, the top edge will slope downwards towards the outer side, the difference in height between the two ends of the top edge being approximately 2–3 mm.

The material of the end tabs should be non-toxic and for comfort will desirably be a soft, flexible polymeric material, e.g. a synthetic rubber or plastic. Conveniently, the end portions and the interconnecting portion may be formed as a single unit from a suitable non-toxic polymeric material. For example, a particularly preferred polymeric material for construction of a device of the present invention is silastic, which is often used in surgery because it is harmless to tissues. By using materials of varying flexibility, devices of identical dimensions, but with different nostril dilating ability may be obtained. The material or materials of such a device will, however, generally be chosen so that it is very light, preferably only about 1 gram or less.

There are large variations amongst adults in height and length of the nose, but the distance between the nasal side walls of adults is fairly constant. For most noses, a suitable length for the connecting member between the two end tabs will generally be about 3.5–5.5 cm.

As noted above, preferably this portion will be thinner at each end than in the central region. Thus, the thickness will generally vary from about 0.5–1 mm to about 2–4 mm in the central region. Most preferably, the end tabs will be displaced from each other by a connecting member having two hinge sections separated by a thicker central region. Thus, for example, the connecting member may have at either end a short-curved hinge section, e.g. of about 0.5 cm, with the concave surface of each hinge region abutting on to the nasal side wall-contacting face of the adjacent end tab. In this case, the dimensions of the hinge regions and the central region of the connecting member will be such that when the device is inserted into the nose the bending of the central region is minimized and most of the bending movement is taken by the hinge regions. By using this form of connecting member, a nasal device is obtained which will fit with comfort into a range of noses depsite small variations in length between the nasal side walls.

Generally, the connecting member will be substantially uniform in width. Thus, if the connecting member is formed of a soft polymeric material such as silastic, it will typically be about 4–5 mm in width along the entire length. In the case of use of a stiffer material, e.g. a stiff plastic, this width may be reduced. Thus, the connecting member may be in the form of a thin thread.

A device of the type of the present invention, suitable for dilating the anterior part of each nasal cavity of an individual, may be used whenever it is desired to improve nasal breathing capacity. Such devices are especially useful, for example, for asthma sufferers and habitual snorers.

Thus, viewed from another aspect, there is disclosed herein a method of improving nasal breathing wherein a device of the present invention capable of dilating the anterior part of each nasal cavity is positioned in the nose.

According to yet another aspect, there is provided a method of reducing or preventing snoring wherein such a device is employed in the same way.

A device of the present invention may also be used as a means for nasally administering a drug. Thus, the end tabs may bear a drug or drug formulation. The drug or drug formulation may, for example, impregnate the end tabs or alternatively may be present in one or more surface cavities or as a coating. One or more surface drug holders in the form of surface indentations or raised wall cavities may, for example, be provided on the nasal side wall-contacting face of each end tab suitable for administration of a drug via absorption across the nasal wall surface into the blood. One or more surface drug holders selected from surface indentations, raised wall cavities or pockets may additionally or alternatively be provided on the non-nasal side wall contacting face of each end tab. Such holders may be employed for administration of drugs, e.g. volatile drugs, by inhalation.

In the case of nasal drug delivery devices of the present invention provided with drug containers in the form of surface indentations or raised wall cavities, these will generally be substantially circular, e.g. about 2–3 mm in diameter. In the case of provision of at least one raised wall cavity on the nasal side wall contacting face of each end tab, these drug containers will preferably be accompanied by small circular protruberances or suction cups as hereinbefore described of substantially the same height, e.g. about 1 mm, and substantially uniformly distributed over the remainder of the same end tab faces.

It is particularly preferred to provide on end tabs having a tapering section extending below the connecting member a drug container in the form of a pocket located at the bottom of the non-nasal side wall contacting face. Such a drug holder will preferably be in the form of a semi-spherical protruberance having an upper aperture, e.g. maximally extending outwards from the non-nasal side wall contacting face of the end tab by about 2–3 mm. Such end tabs may preferably additionally have at least one raised wall cavity on the nasal side wall-contacting face as described above and will most desirably be of curved form.

For incorporation in surface indentations, raised wall cavities or pockets of a drug-delivery device of the present invention or formation of a drug-containing coating on the end tabs of such a device, a drug will generally be employed in a gradual release form. For example, a drug for this purpose may be mixed with a fixing agent which melts slowly at the normal temperature of the nasal cavities, for example, white chocolate, or it may be in crystalline form and evaporated by the warmth of the nasal wall and the expired humid air from the lungs.

Thus, viewed from a still further aspect, there is disclosed herein a method of nasally administering a drug wherein a device according to the present invention having end tabs bearing said drug or a formulation comprising said drug is positioned in the nose.

A nasal drug delivery device of this type, which when in use enables improved nasal breathing capacity, is particularly desirable for administration of anti-asthmatic drugs of the $\beta_2$-adrenoceptor agonist or corticosteroid type. These drugs are commonly administered by oral inhalation. However, this manner of administion has the drawback that generally only 5–10% of the drug administered actually reaches the bronchi, since much of the dose is deposited in the throat. Furthermore, some asthma suffers are unable to aquire the technique for use of an oral aerosol spray. Using a nasal drug delivery device of the present invention, an anti-asthmatic drug of the $\beta_2$-adrenoceptor agonist or corticosteroid type can be administered efficiently and very conveniently over several minutes or several hours.

Nasal drug delivery devices of the present invention have far wider applicability than in the treatment of asthma. Such devices may be used to administer any drug which is absorbed across the nasal/bronchial mucosa and is effective in low doses, e.g. less than one milligram, or any drug for local treatment in the nasal cavities. Hormones such as insulin, growth hormone and anti-diuretic hormone, which cannot be taken orally because of their susceptibility to attack by proteolytic enzymes of the digestive tract may, for example, be administered in this way. Examples of drugs for local treatment in the nasal cavities which may also be administered by means of a drug-delivery device as hereinbefore described include nasal decongestants. Using such a device rather than a nasal spray, a decongestant can be better distributed in the nasal cavities and, if desired, administered continually over a long period. Further, some immediate relief may be obtained upon insertion of the device as a result of dilation of the anterior part of each nasal cavity.

A particularly important advantage of a drug delivery device of the present invention is that it can be used to administer a pre-determined dose of a drug to an individual even while asleep. This is well illustrated by consideration of the problems of asthma sufferers. Most asthma sufferers have more trouble with their breathing during the night than during the day. Before retiring to bed, an asthma sufferer may reduce his liability to develop asthma symptoms in his sleep by inserting an anti-asthmatic drug delivery device of the present invention, desirably a device capable of releasing an effective amount of an anti-asthmatic drug over several hours. Use of a simpler nasal device as provided by the present invention to just improve nasal breathing capacity overnight may also be beneficial, particularly if the asthma sufferer has a cold and is therefore more liable to breathe orally.

Specific embodiments of nasal devices according to the present invention incorporating some of the features discussed above will hereinafter be described by way of example with reference to the accompanying drawings wherein:

FIG. 5 shows a perspective view of a preferred nasal drug delivery device of the present invention suitable for a male adult nose (scale 100:154);

FIG. 6 is an end view of an end tab of the device of FIG. 5;

FIG. 7 is a side view of the device of FIG. 5;

FIG. 8 shows a plan view of the device of FIG. 5 with the concave, i.e. non-nasal side wall contacting faces of the end tabs uppermost;

Figure 1:
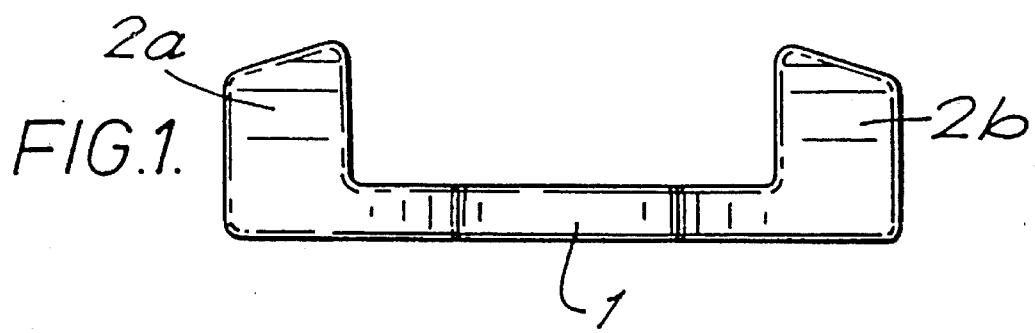
FIG. 1 is a plan view of a device for improving nasal breathing capacity with the non-nasal side wall-contacting faces of the end tabs uppermost.
Figure 2:
FIG. 2 is a side view of the device of FIG. 1.
Figure 3:
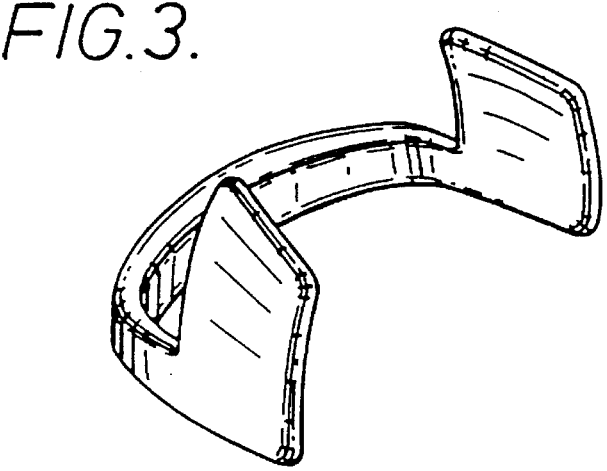
FIG. 3 illustrates the device of FIG. 1 in the bent form ready for insertion into the nasal cavities.

Referring firstly to FIGS. 1 to 3, the device is formed as a single-unit from a non-toxic, soft, flexible polymeric material, e.g. silastic. The two end portions 2a,2b are in the form of gently curved tabs, about 1 mm in thickness and about 10 mm wide, interconnected by a resilient connecting member 1, about 3.5 cm long, about 4–5 mm wide and varying in thickness from about 1 mm at either end to about 2 mm in the central region. The top edge of each end tab slopes downwards towards the outer side, the difference in height between he two ends of the top edge being about 2–3 min. As stated above, there are large variations amongst adults in height and length of the nose, but the distance between the nasal side walls of adults is fairly constant. The dimensions of the illustrated device have been chosen so that it will be suitable for use in a wide range of adult noses, e.g. to alleviate snoring. When the device is correctly inserted into a normal adult nose with the connecting member bent so that the concave faces of the end tabs are towards each other, the end tabs will extend about 15–17 mm into the nasal cavities and will be retained in the nasal cavities resting on skin below the mucosa with their convex faces in contact with the nasal side walls. In an equivalent device for a young child, the length of the connecting member will be shorter and the end tabs smaller in area. In many habitual snorers deformities in the nose have been found to be an important factor accounting for their tendency to snore and for such individuals the shapes of the end tabs may need to be modified.

Figure 4:
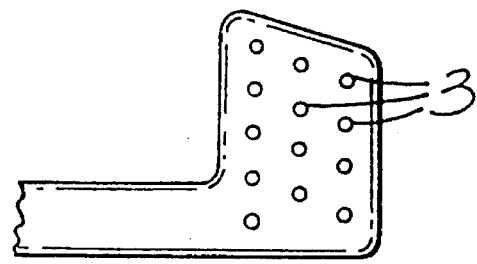
FIG. 4 shows the non-nasal side wall contacting face of an end tab of a drug-delivery device based on the device as shown in FIGS. 1 to 3.
Figure 9:
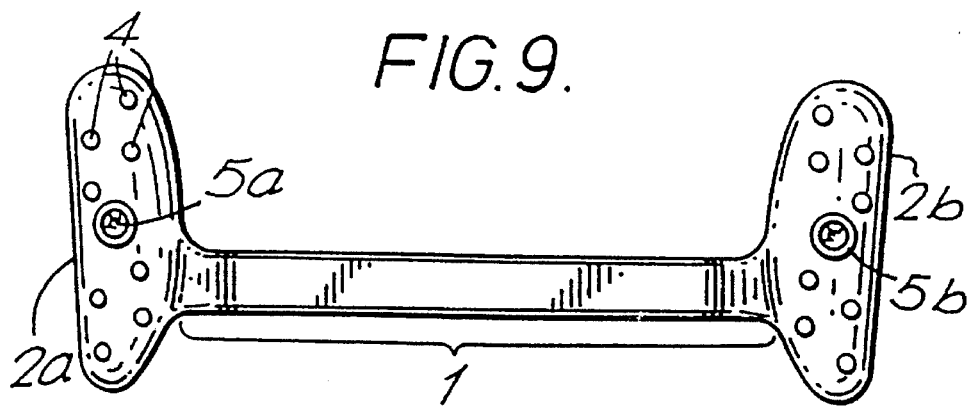
FIG. 9 shows a plan view of the device of FIG. 5 with the convex, nasal side wall contacting faces of the end tabs uppermost.

Referring to the end portion of the nasal drug-delivery device illustrated in FIG. 4, this device is identical to the device shown in FIGS. 1 to 3, except that the concave non-nasal side wall contacting face of each end tab has a plurality of surface indentations 3 for holding a drug or drug formulation, e.g. a drug mixed with a fixing agent which melts slowly at the normal temperature of the nasal cavities. Depending on the fixing agent and the number and shape of the indentations, the release time of the drug may vary from a few minutes to a number of hours (e.g. 10 hours).

The more preferred nasal drug delivery device illustrated by FIGS. 5 to 9 and 11 which is intended for use in nasally administering drugs to human males, is also formed as a single unit from a nontoxic, soft, flexible polymeric material with two end portions 2a, 2b in the form of thin curved tabs of about 10 mm in maximum width and having a thickness and maximum depth of curvature of about 1–2 min. The length of the end tabs 2a, 2b are such that when correctly positioned in the nasal cavities of a human male nose with the convex faces against the nasal side walls, each end tab extends into its respective nasal cavity by about 20 mm so that the top convexly-curved edge is below the sensitive nasal mucosa and the bottom tapering section of each end tab, extending below the interconnecting resilient member 1 by about 7 mm, engages with the floor of the nasal cavity. Retention of the device in the nostrils depends principally upon the pressure exerted outwards by the end tabs 2a,2b against the nasal side walls, but is assisted by the contact of the bottom of each end tab with the floor of the respective nasal cavity and also by small protruberances 4 of about 1 mm in height and diameter provided on the nasal side wall-contacting faces of the end tabs.

Sited at the central region of the convex face of each end tab is a raised wall cavity 5a,5b, about 2–3 mm in diameter and about 1 mm in height, suitable for use in administering a drug via absorption across the nasal side wall surface. Such a device can, however, additionally be employed for administration of a drug by inhalation by use of the substantially half-spherical pockets 6a,6b with upper aperture 7a,7b, which extend maximally outwards at the bottom of the concave face of each end tab by about 2–3 mm. A drug for incorporation in either of the types of drug container will generally be in a gradual release form. Thus, the pockets 6a,6b may, for example, contain a β-adrenoceptor agonist in combination with a fixing agent which melts slowly at the normal temperature of the nasal cavities, while the raised wall cavities 5a,5b may, for example, be employed for adminstration of a hormone across the nasal side wall surface into the blood.

A further important feature of the device illustrated in FIGS. 5–9 is that the connecting member 1 consists of a thicker central region 8 of about 4.5 cm in length and varying in thickness from about 2 mm to about 4 mm at the mid-point sandwiched between two curved hinge sections 9a,9b, each of about 0.5 cm and varying in thickness from about 2 mm to about 0.5–1 mm. The concave surfaces of these hinge sections abutt on to the convex faces of the end tabs 2a,2b, i.e. the nasal side wall contacting surfaces. When the device is fitted into a nose, only the hinge sections 9a,9b of the connecting member together with the end tabs 2a,2b are substantially bent inwards and by virtue of the hinge sections 9a,9b, the device is adapted to deal with small variations between adult male noses in the distance between the nasal side walls. Thus, the extent of inward bending of the hinge sections when the device is fitted will depend upon the distance between the nasal side walls of the patient.

Figure 10:
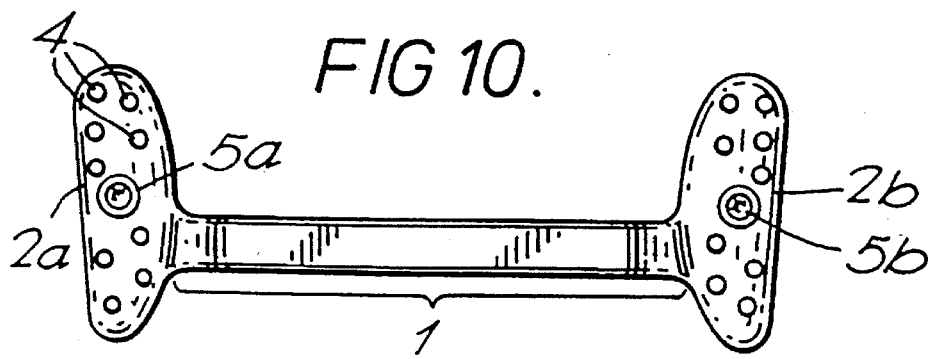
FIG. 10 shows a plan view of a child's version of the device of FIG. 5 (scale 100:154)
Figure 11:
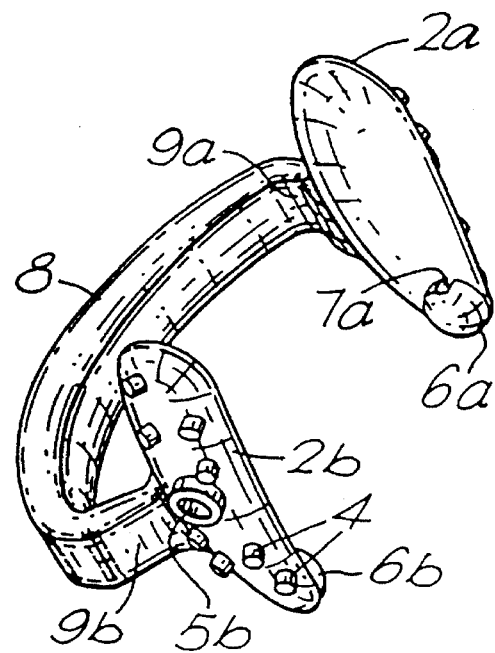
FIG. 11 illustrates the device of FIG. 5 in the bent form ready for insertion into the nasal cavities.

Devices of the same form but with a shorter connecting member 1 and end tabs 2a,2b of smaller area may be constructed for use in smaller noses. Thus, referring to the child's device illustrated in FIG. 10, the connecting member 1 is about 3.5 cm in length with a central region 8 of about 2–4 mm in thickness sandwiched between two much shorter curved hinge sections 9a,9b. These hinge sections are similar to the hinge sections 9a,9b, of the equivalent male adult device described above. The end tabs 2a,2b have a maximum width of about 8 mm and when inserted into an appropriate child's nose with the convex faces towards the side walls should contact the floor of their respective nasal cavity by means of the tip of the tapering bottom section, extending about 4 mm below the connecting member 1, and press outwardly against the nasal side walls below the mucosa. The maximum length of extension of each end tab into its respective nasal cavity will generally be about 15 mm.

Identical devices, except for omission of the drug containers and provision of small protruberances as hereinbefore described at substantially regular intervals over the whole convex face of each end tab, are alternatively highly preferred for use in faciliating nasal breathing when contemporaneous nasal administration of a drug is not desired.

Modifications to the specific devices described and to any broad aspects of nasal devices referred to or suggested herein may be apparent to those skilled in the art and the disclosure hereof is intended to encompass any such modifications. The devices may embody a number of inventions for which protection may be sought. The various broad aspects referred to herein are intended as guides to some specific areas where inventions are presently considered to lie.

I claim:

1. A one-piece device for positioning in the nose comprising:

(i) a pair of tabs for positioning in respective nostrils; and (ii) an elongate connecting member resiliently interconnecting the tabs;

wherein:

(a) each tab is resilient and has a surface for engaging the outer side wall of the respective nostril, is relatively thin se as to project a relatively small distance from the outer side wall into the passage of the respective nostril and is formed from a resilient, relatively soft material whereby said surface may conform to the contours of said respective side wall;

(b) the connecting member is of a length sufficient to follow a path from one tab to the other over the septum of the nose;

(c) said connecting member is resiliently bendable from an inoperative configuration into an operative configuration in which the tabs are positioned within the nostrils, the connecting member follows said path over the septum, and there is a restoring force tending to return said connecting member to the inoperative configuration; and (d) the restoring force is sufficient to maintain the device in the nose of a user by means of engagement of the tabs with their respective nostril by means of the tabs urging the respective side walls outwardly.

2. The device of claim 1, wherein said connecting member is generally straight in the inoperative condition of the device and is bent resiliently to follow a curved path in the operative configuration of the device.

3. The device of claim 2, wherein said connecting member comprises a main relatively thick portion joined to said tabs by relatively thin hinge portions.

4. The device of claim 3, wherein the hinge portions taper in thickness from the main portion to the tabs.

5. The device of claim 3, wherein said main portion tapers in thickness from its center to said respective hinge portions.

6. The device of claim 3, wherein in the inoperative condition the tabs are displaced by the hinge portions away from the axis of the main portion of the connecting member.

7. The device of claim 1, wherein the surface of each tab which engages the nostril side wall is convex.

8. The device of claim 1, wherein each tab is curved in both a longitudinal and a lateral direction.

9. The device of claim 1, wherein each tab has a tapering lower portion.

10. The device of claim 9, wherein the tapering lower portion has a hollow protrusion on the side remote from the nostril side wall, said protrusion having an opening to permit the dispensing of a medication from within the protrusion.

11. The device of claim 10, wherein said protrusion is semispherical.

12. The device of claim 1, wherein each tab is elongated, extends transversely to said connecting member and has a first relatively short portion extending on one side of said connecting member to enable contact with the floor of the nasal cavity, and a second relatively long portion extending on the other side of said connecting member.

13. The device of claim 1, wherein the surface of each tab which engages the nostril side wall is provided with gripping means.

14. The device of claim 13, wherein said gripping means comprises a plurality of protuberances.

15. The device of claim 1, wherein the surface of each tab which engages the nostril side wall is provided with a cavity having an opening to permit the dispensing of a medication from within the cavity.

16. The device of claim 15, wherein said cavity is defined by a raised wall extending from said surface.

17. A one-piece device for positioning in the nose comprising:

(i) a pair of tabs for positioning in respective nostrils; and (ii) a resilient elongated connecting member interconnecting the tabs;

wherein:

(a) each tab is resilient and has a surface for engaging the outer side wall of the respective nostril, is relatively thin so as to project a relatively small distance from the outer side wall into the passage of the respective nostril;

(b) the connecting member is of a length sufficient to follow a path from one tab to the other over the septum of the nose, and comprises a relatively thick main portion connected at its end to said tabs by thinner hinge portions;

(c) said connecting member is resiliently bendable from an inoperative configuration into an operative configuration in which the tabs are positioned within the nostrils, the connecting member follows said path over the septum, and there is a restoring force tending to return said connecting member to the inoperative configuration;

(d) the arrangement of said relatively thick main portion and the said thinner hinge portions of said connecting member being such that in said operative condition, bending of the said main portion is minimized and most of the bending movement is taken by said hinge portions; and (e) the restoring force is sufficient to maintain the device in the nose of a user by means of engagement of the tabs with their respective nostril outer side wall, and to dilate the nostrils by means of the tabs urging the respective side walls outwardly.

18. A one-piece device for positioning in the nose comprising:

(i) a pair of tabs for positioning in respective nostrils; and (ii) a resilient elongated connecting member interconnecting the tabs;

wherein:

(a) each tab is resilient and has a surface for engaging, the outer side wall of the respective nostril, and is relatively thin so as to project a relatively small distance from the outer side wall into the passage of the respective nostril;

(b) the connecting member is of a length sufficient to follow a path from one tab to the other over the septum of the nose, and comprises a main portion connected at its ends to said tabs by hinge portions;

(c) said connecting member is resiliently bendable from an inoperative configuration in which said main portion is generally straight, into an operative configuration in which the tabs are positioned within the nostrils and in which said main portion is bowed, the connecting member follows said path over the septum, and there is a restoring force tending to return said connecting member to the inoperative configuration; and (d) the restoring force is sufficient to maintain the device in the nose of a user by means of engagement of the tabs with their respective nostril outer side walls, and to dilate the nostrils by means of the tabs urging the respective side walls outwardly.

19. A one-piece device for positioning in the nose comprising:

(i) a pair of tabs for positioning in respective nostrils; and (ii) a resilient elongated connecting member interconnecting the tabs;

wherein:

(a) each tab is elongated, resilient and has a surface for engaging the outer side wall of the respective nostril, is relatively thin so as to project a relatively small distance from the outer side wall into the passage of the respective nostril, extends transversely to the axis of the connecting member and is formed from a relatively soft material whereby said surface may conform to the contours of the respective outer side wall;

(b) the connecting member is of a length sufficient to follow a path from one tab to the other over the septum of the nose, and comprises a relatively thick main portion connected at its ends to said tabs by relatively thin hinge portions;

(c) said connecting member is resiliently bendable from an inoperative configuration in which said main portion is generally straight, into an operative configuration in which the tabs are positioned within the nostrils and in which said main portion is bowed, the connecting member follows said path over the septum, and there is a restoring force tending to return said connecting member to the inoperative configuration;

(d) the arrangement of said relatively thick main portion and the said thinner hinge portions of said connecting member being such that in said operative condition, bending of the said main portion is minimized and most of the bending movement is taken by said hinge regions and such that said tabs are offset from the axis of said main portion by said hinge portions; and (e) the restoring force is sufficient to maintain the device in the nose of a user by means of engagement of the tabs with their respective nostril outer side walls, and to dilate the nostrils by means of the tabs urging the respective side walls outwardly.

20. A device for positioning in the nose to administer medication comprising:

(i) a pair of tabs for positioning in respective nostrils; and (ii) an elongated connecting member resiliently interconnecting the tabs;

wherein:

(a) each tab is resilient and has a surface for engaging the outer side wall of the respective nostril, is relatively thin so as to project a relatively small distance from the outer side wall into the passage of the respective nostril and is formed from a resilient, relatively soft material whereby said surface may conform to the contours of said respective side wall;

(b) the connecting member is of a length sufficient to follow a path from one tab to the other over the septum of the nose;

(c) said connecting member is resiliently bendable from an inoperative configuration into an operative configuration in which the tabs are positioned within the nostrils, the connecting member follows said path over the septem, and there is a restoring force tending to return said connecting member to the inoperative configuration; and (d) the restoring force is sufficient to maintain the device in the nose of a user by means of engagement of the tabs with their respective nostril outer side walls, and to dilate the nostrils by means of the tabs urging the respective side walls outwardly; and (e) said tabs are provided with means for retaining a medication to be administered.

21. The device of claim 20 wherein the surface of each tab which engages the nostril side wall is provided with a cavity having an opening to permit the dispensing of medication from within the cavity.

22. The device of claim 21 wherein the surface of each tab which is remote from the nostril side wall is provided with a cavity having an opening to permit the dispensing of medication from within the cavity.

23. A method for improving nasal breathing comprising the step of positioning in the nose a device comprising:

(i) a pair of tabs for positioning in respective nostrils; and (ii) an elongated connecting member resiliently interconnecting the tabs;

wherein:

(a) each tab is resilient and has a surface for engaging the outer side wall of the respective nostril, is relatively thin so as to project a relatively small distance from the outer side wall into the passage of the respective nostril and is formed from a resilient, relatively soft material whereby said surface may conform to the contours of said respective side wall;

(b) the connecting member is of a length sufficient to follow a path from one tab to the other over the septum of the nose;

(c) said connecting member is resiliently bendable from an inoperative configuration into an operative configuration in which the tabs are positioned within the nostrils, the connecting member follows said path over the septum, and there is a restoring force tending to return said connecting member to the inoperative configuration; and (d) the restoring force is sufficient to maintain the device in the nose of a user by means of engagement of the tabs with their respective nostril outer side walls, and to dilate the nostrils by means of the tabs urging the respective side walls outwardly.

24. A method for improving nasal breathing comprising the step of positioning in the nose a device comprising:

(i) a pair of tabs for positioning in respective nostrils; and (ii) a resilient elongated connecting member interconnecting the tabs;

wherein:

(a) each tab is elongated, resilient and has a surface for engaging the outer side wall of the respective nostril, is relatively thin so as to project a relatively small distance from the outer side wall into the passage of the respective nostril, extends transversely to the axis of the connecting member and is formed from a relatively soft material whereby said surface may conform to the contours of the respective side wall;

(b) the connecting member is of a length sufficient to follow a path from one tab to the other over the septum of the nose, and comprises a relatively thick main portion connected at its ends to said tabs by relatively thin hinge portions;

(c) said connecting member is resiliently bendable from an inoperative configuration in which said main portion is generally straight, into an operative configuration in which tabs are positioned within the nostrils and in which said main portion is bowed, the connecting member follows said path over the septum, and there is a restoring force tending to return said connecting member to the inoperative configuration;

(d) the arrangement of said relatively thick main portion and the said thinner hinge portions of said connecting member being such that in said operative condition, bending of the said main portion is minimized and most of the bending movement is taken by said hinge regions and such that said tabs are offset from the axis of said main portion by said hinge portions; and (e) the restoring force is sufficient to maintain the device in the nose of a user by means of engagement of the tabs with their respective nostril outer side walls, and to dilate the nostrils by means of the tabs urging the respective side walls outwardly.

25. A method of reducing or preventing snoring comprising the step of positioning in the nose a device comprising:

(i) a pair of tabs for positioning in respective nostrils; and (ii) an elongated connecting member resiliently interconnecting the tabs;

wherein:

(a) each tab is resilient and has a surface for engaging the outer side wall of the respective nostril, is relatively thin so as to project a relatively small distance from the outer side wall into the passage of the respective nostril and is formed from a resilient, relatively soft material whereby said surface may conform to the contours of said respective side wall;

(b) the connecting member is of a length sufficient to follow a path from one tab to the other over the septum of the nose;

(c) said connecting member is resiliently bendable from an inoperative configuration into an operative configuration in which the tabs are positioned within the nostrils, the connecting member follows said path over the septum, and there is a restoring force tending to return said connecting member to the inoperative configuration; and (d) the restoring force is sufficient to maintain the device in the nose of a user by means of engagement of the tabs with their respective nostril outer side walls, and to dilate the nostrils by means of the tabs urging the respective side walls outwardly.

26. A method of administering a medication nasally comprising the step of positioning in the nose a device comprising:

(i) a pair of tabs for positioning in respective nostrils; and (ii) an elongated connecting member resiliently interconnecting the tabs;

wherein:

(a) each tab is resilient and has a surface for engaging the outer side wall of the respective nostril, is relatively thin so as to project a relatively small distance from the outer side wall into the passage of the respective nostril and is formed from a resilient, relatively soft material whereby said surface may conform to the contours of said respective side wall;

(b) the connecting member is of a length sufficient to follow a path from one tab to the other over the septum of the nose;

(c) said connecting member is resiliently bendable from an inoperative configuration into an operative configuration in which the tabs are positioned within the nostrils, the connecting member follows said path over the septum, and there is a restoring force tending to return said connecting member to the inoperative configuration;

(d) the restoring force is sufficient to maintain the device in the nose of a user by means of engagement of the tabs with their respective nostril outer side walls, and to dilate the nostrils by means of the tabs urging the respective side walls outwardly; and (3) said tabs are provided with means retaining a medication to be administered.

27. The method of claim 26 wherein said medication is retained in a cavity provided on the surface of the tab which engages the nasal wide wall.

28. The method of claim 26 wherein said medication is retained in a cavity provided on the surface of the tab remote from the nostril side wall.

* * * * *